United States Patent
Fukushima

[11] Patent Number: 5,528,492
[45] Date of Patent: Jun. 18, 1996

[54] METHOD OF MANAGING MEDICAL DIAGNOSTIC DATA WITH REFERENCE RELATIONSHIP

[75] Inventor: Yuki Fukushima, Tochigiken, Japan

[73] Assignee: Kabushiki Kaisha Toshiba, Tokyo, Japan

[21] Appl. No.: 942,163

[22] Filed: Sep. 4, 1992

[30] Foreign Application Priority Data

Sep. 6, 1991 [JP] Japan .................................. 3-226695

[51] Int. Cl.⁶ .............................................. G06F 159/00
[52] U.S. Cl. ................................................ 364/419.19
[58] Field of Search ............... 364/413.02, 200 MS File, 364/900 MS File, 413.13, 413.24, 419, 419.19, 419.07; 128/653.1; 358/439, 458; 382/2, 4, 6

[56] References Cited

U.S. PATENT DOCUMENTS

| | | | |
|---|---|---|---|
| 4,847,694 | 7/1989 | Nishihara | 358/434 |
| 4,864,500 | 9/1989 | Ichihara | 364/413.24 |
| 4,958,283 | 9/1990 | Tawara et al. | 364/413.13 |
| 5,095,906 | 3/1992 | Ema | 128/653.1 R |
| 5,132,900 | 7/1992 | Gilschrist et al. | 364/419.19 |
| 5,140,518 | 8/1992 | Ema | 364/413.01 |
| 5,204,812 | 4/1993 | Kasiraj et al. | 364/419.19 |

Primary Examiner—Gail O. Hayes
Assistant Examiner—Frantzy Poinvil
Attorney, Agent, or Firm—Oblon, Spivak, McClelland, Maier & Neustadt

[57] ABSTRACT

A method of managing medical diagnostic data in a database system, capable of simplifying the data look up operation to be made at a user terminal while working on a currently interested medical diagnostic data. In the method, one of the medical diagnostic data stored in the database is specified as a base data while a desired number of the medical diagnostic data stored in the database are specified as reference data of the base data, and the identification data of the base data is stored in correspondence with identification data of the reference data in the database. Then, the base data is presented on a user terminal along with the identification data of the reference data stored in correspondence with the identification data of the data base, such that when one of the identification data for a desired one of the reference data is specified on the user terminal, the desired one of the reference data corresponding to the specified one of the identification data can be presented on the user terminal.

15 Claims, 13 Drawing Sheets

| MEDICAL EXAMINATION ID | REFERENCE DATA ID |
|---|---|
| E 0 0 0 5 1 3 | E 0 0 0 2 9 4 - I 1 |
| E 0 0 0 5 1 3 | E 0 0 0 2 9 4 - I 2 |
| E 0 0 0 5 1 3 | E 0 0 0 3 3 0 |
| E 0 0 0 5 1 3 | E 0 0 0 2 9 4 - R 1 |
| E 0 0 0 5 1 3 | P 0 0 1 3 2 7 - C 1 |
| E 0 0 0 5 1 3 | B 0 8 9 6 1 2 - P 1 3 5 |

FIG.6

| MEDICAL EXAMINATION ID | NO. | IMAGE A | IMAGE B | IMAGE C | IMAGE D |
|---|---|---|---|---|---|
| E000513 | 1 | E000294-I1 | E000264-I2 | E000513-I1 | E000513-I2 |
| E000513 | 2 | E000330-I1 | E000330-I2 | E000513-I1 | E000513-I2 |
| E000513 | 3 | E000330-I3 | E000330-I4 | E000513-I1 | E000513-I2 |
| E000514 | 1 | E000514-I1 | E000514-I2 | E000514-I3 | E000037-I1 |

FIG.7

| REFERENCE DATA ID | FLAG |
|---|---|
| E000105 | |
| E000106 | |
| E000294 | ON |
| E000295 | |
| E000330 | |

FIG.9

| REFERENCE DATA ID | TIME COUNTER |
|---|---|
| E000294-I1 | 60 |
| E000330 | 45 |
| E000294-I2 | 40 |
| E000294-R1 | 40 |

FIG.12

| DATA NAME | (ID) | DATE | DOCTOR |
|---|---|---|---|
| CHEST X-RAY (FRONT) | (E000294) | 1990. 3.15 | |
| CHEST X-RAY (SIDE) | (E000294) | 1990. 3.15 | |
| CHEST X-RAY CONTRAST | (E000330) | 1990. 3.16 | |
| DIAGNOSTIC REPORT | (E000294) | 1990. 3.15 | (RADIOLOGY) SATO |
| CLINCAL CHART | (P001327) | | (INTERNAL) SUZUKI |
| MEDICAL REFERENCE DOCUMENT (CHEST X-RAY IMAGE READING) | (B089612) | | |

METHOD OF MANAGING MEDICAL DIAGNOSTIC DATA WITH REFERENCE RELATIONSHIP

BACKGROUND OF THE INVENTION

1. Field of the Invention

The present invention relates to a method of managing medical diagnostic data registered in a database system such as a database sharing network.

2. Description of the Background Art

A database sharing network is a network in which a database storing a number of registered data is shared among a plurality of users operating a plurality of terminal work stations connected to the database through communication lines.

The database can register data in various forms including image data and text data. In such a database sharing network, in order to obtain the desired data from the database, it is necessary for the user to make an access to the network through the terminal work station and carry out the prescribed data look up operation on the terminal work station. The prescribed data look up operation normally includes either the input of the identification data of the desired data, such as an ID code assigned to the desired data or a data name of the desired data, at the terminal work station by using a keyboard or the specifying of the desired data on the identification data menu displayed on the terminal work station by using a pointing device.

Such a database sharing network is particularly useful for managing medical diagnostic data, where a doctor can produce a new diagnostic report according to the medical examination results, medical diagnostic images such as X-ray images and tomographic images, and clinical chart of a specific patient, by utilizing the registered data of the database sharing network such as the other medical examination results, other medical diagnostic images, medical reference documents, other clinical charts, and other diagnostic reports, as the reference data. Here, such reference data utilized in producing the new diagnostic report may be written into the new diagnostic report in terms of their identification data. The new diagnostic report produced by using the database sharing network will then be registered in the database as the data that can be looked up later on by the same doctor who have produced this diagnostic report or by any other doctors using the database sharing network as the reference data.

In addition, such a database sharing network can also be utilized in holding a conference among a plurality of doctors using the database sharing network equipped with appropriate conference terminal devices. In such a case, a host doctor selects the necessary ones of the registered data to be used during the conference in advance, such that the necessary data can be presented to the participants of the conference through the conference terminal devices connected to the database sharing network, according to the data look up operations made by the host doctor.

Now, in such a conventional database sharing network, when the user wishes to look up the particular reference data that had been looked up before while working on a particular currently interested data, it is necessary for the user to repeat the same data look up operation for that particular reference data again, and such repetitive data look up operations can be quite time consuming and cumbersome to the users.

In particular, in the database sharing network for the medical diagnostic data, the doctor using the database sharing network for the purpose of working on a particular currently interested medical diagnostic data frequently encounters the situation in which it is necessary to look up the same reference data for a number of times during a single diagnostic session, such that these repetitive data look up operations are not only cumbersome things to do on the user terminal by himself but also painfully time consuming as a considerable amount of time is required for making such operations on the user terminal as well as for obtaining the desired data on the user terminal from the database sharing network in response to such operations, while the period for a single diagnostic session is usually very limited and the time consumed in conjunction with the repetitive data look up operations considerably reduces the time available for the doctor to carry out the other diagnostic activities.

SUMMARY OF THE INVENTION

It is therefore an object of the present invention to provide a method of managing medical diagnostic data in a database system, capable of simplifying the data look up operation to be made at a user terminal while working on a currently interested medical diagnostic data, so as to enable the doctor using the database system to conduct the diagnostic session more efficiently, especially when the diagnostic session requires the repetitive data look up operations.

According to one aspect of the present invention, there is provided a method of managing medical diagnostic data in a database system, comprising the steps of: (a) storing medical diagnostic data in a database of the database system; (b) specifying one of the medical diagnostic data stored in the database at the step (a), as a base data; (c) specifying a desired number of the medical diagnostic data stored in the database at the step (a), as reference data of the base data specified at the step (b); (d) storing an identification data of the base data specified at the step (b) in correspondence with identification data of the reference data specified at the step (c), in the database; (e) presenting the base data specified at the step (b) on a user terminal of the database system, along with the identification data of the reference data stored in correspondence with the identification data of the data base at the step (d); (f) specifying one of the identification data for a desired one of the reference data presented along with the base data on the user terminal; and (g) presenting the desired one of the reference data corresponding to said one of the identification data specified at the step (f) on the user terminal.

According to another aspect of the present invention, there is provided an apparatus for managing medical diagnostic data in a database system, comprising: database for storing medical diagnostic data in a database, where one of the medical diagnostic data stored in the database is specified as a base data, and a desired number of the medical diagnostic data stored in the database are specified as reference data of the base data; reference data table means for storing an identification data of the base data stored in the database, in correspondence with identification data of the reference data stored in the database; means for requesting a presentation of the base data stored in the database; means for searching the base data requested by said means for requesting in the database, and the identification data of the reference data stored in said reference data table means; and means for presenting the base data searched by said means for searching, along with the identification data of the reference data searched by said means for searching.

Other features and advantages of the present invention will become apparent from the following description taken in conjunction with the accompanying drawings.

BRIEF DESCRIPTION OF THE DRAWINGS

FIG. 6 is an exemplary illustration of another example of a reference data table to be registered in the database in the procedure of database registration according to the flow chart of FIG. 4.

FIG. 7 is an exemplary illustration of one example of a work table to be utilized in generating the reference data table of FIG. 5.

FIG. 9 is an exemplary illustration of another example of a work table to be utilized in generating the reference data table of FIG. 5.

FIG. 12 is an exemplary illustration of one example of a reference data menu to be utilized in the procedure of reference data checking according to the flow chart of FIG. 11.

DETAILED DESCRIPTION OF THE PREFERRED EMBODIMENTS

Figure 1:
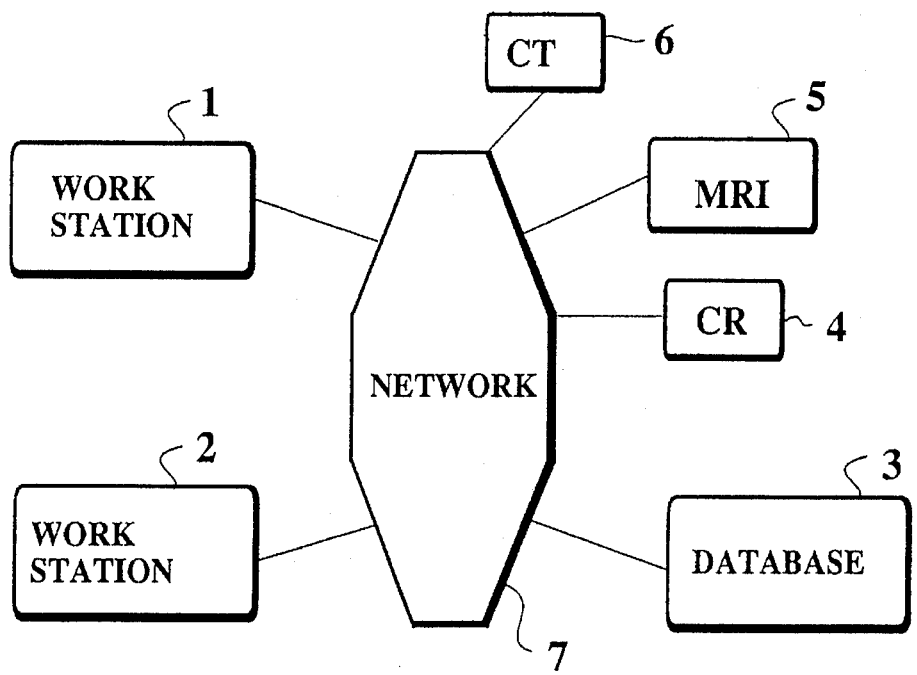
FIG. 1 is a schematic block diagram of a database sharing network for implementing one embodiment of a method of managing medical diagnostic data according to the present invention.

Referring now to FIG. 1, a database sharing network as an example of a database system for implementing one embodiment of a method of managing medical diagnostic data according to the present invention will be described in detail.

This database sharing network of FIG. 1 comprises: work stations 1 and 2 which function as user terminals; a database 3 for storing medical diagnostic data; and various modality such as a computed radiology device (CR) 4, a magnetic resonance imaging device (MRI) 5, and a computed tomography device (CT) 6; all of which are connected through a network 7. This database sharing network is controlled by a database management system (DBMS) (not shown) provided inside the database 3. Here, any desired number of the work stations other than two as shown in FIG. 1 may be connected to the network 7, and any other desired modality other than those shown in FIG. 1 may be connected to the network 7.

In this embodiment, the database 3 registers the various medical diagnostic data such as medical examination results, medical diagnostic images such as X-ray images and tomographic images, medical reference documents, clinical charts, diagnostic reports, all of which can be looked up from any one of the work stations as base data or reference data. Here, the DBMS generates an index table for listing the identification data such as data IDs or data names of the registered medical diagnostic data, and such an index table is also registered in the database 3.

In this embodiment, the producing of a new diagnostic report by utilizing the reference data, on the database sharing network of FIG. 1, is carried out according to the flow chart of FIG. 2, as follows.

As an example, a case in which a radiologist produces a new diagnostic report at the work station 1 according to the image reading of a particular medical examination result assigned with a medical examination ID of E000513 will be considered.

In this case, at first, the particular medical examination result assigned with the medical examination ID of E000513 is displayed on the work station 1 at the step 111, for the purpose of the image reading by the radiologist.

Figure 3:
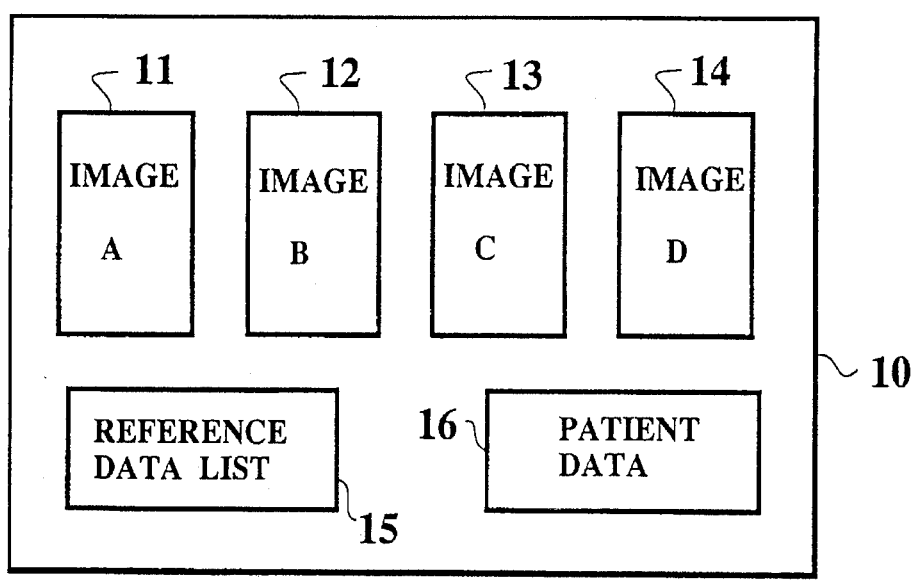
FIG. 3 is a schematic illustration of an exemplary image display on a work station in the procedure of image reading according to the flow chart of FIG. 2.

Then, at the step 112, in response to a reference request command entered by the radiologist at the work station 1, the work station 1 displays an image display 10 as shown in FIG. 3, which includes image windows 11 to 14 for showing images A to D of the selected number (four in this case) of the reference data, a reference data list 15 enlisting the identification data of the available reference data, and a patient data indicating useful information on a patient who is the subject of the particular medical examination.

Then, at the step 113, whether the image reading is finished or not is inquired. In a case the radiologist indicates that the image reading is finished, the process proceeds to the step 118 to be described below, whereas otherwise the process proceeds to the step 114 at which the radiologist specifies a desired reference data either by selecting desired one of the identification data enlisted on the reference data list 15 or by entering the identification data of the desired reference data so as to request the search of the desired reference data in the database 3. For example, the medical diagnostic image and the diagnostic report of the medical examination E000294, the medical examination result of the medical examination E000330, the clinical chart of the patient P001327, and the medical reference document B089612 concerning the image reading of the chest portion X-ray image can be selected as the desired reference data by the radiologist.

Then, at the step 115, whether any reference data is specified at the step 114 or not is determined. In case there is no reference data specified at the step 114, the process proceeds to the step 113 described above, whereas otherwise the process proceeds to the step 116 at which the DBMS controls the database sharing network of FIG. 1 to carry out the requested search in the database 3 and display the desired reference data specified at the step 114 on the work station 1.

Then, at the step 117, the radiologist produces the diagnostic report on the medical examination result of the medical examination E000513, by utilizing these reference data displayed on the work station 1. Here, for example, the radiologist may actually utilize the first and second medical diagnostic images and the diagnostic report of the medical examination E000294, the medical examination result of the medical examination E000330, the clinical chart of the patient P001327, and the page 135 of the medical reference document B089612 concerning the image reading of the chest portion X-ray image. The process then returns to the step 113 described above.

Then, when the radiologist indicates that the image reading is finished at the step 113, next at the step 118, the radiologist inputs the IDs of the reference data actually utilized in producing the diagnostic report at the step 117, such as E000294-I1, E000294-I2, E000294-R1, E000330, P001327-C1, B089612-P135, and in response the DBMS registers the IDs of these reference data into the database 3 in correspondence with the ID of the produced diagnostic report, such that the produced diagnostic report can be regarded as the base data of these reference data from which any one of the reference data can be looked up, as will be described in detail below.

Finally, at the step 119, whether the next image reading is necessary or not is inquired. In case the radiologist indicates that the next image reading is necessary, the process returns to the step 111 described above so as to carry out the next image reading, whereas otherwise the process terminates.

In this procedure, at the step 118, the registration of the ID of the produced diagnostic report and the inputted reference data IDs can be made according to the flow chart of FIG. 4, as follows.

Namely, as the registration process starts at the step 31 on the work station 1 side, the radiologist operates the work station 1 to send a registration request at the step 32.

Figures 4, 5:
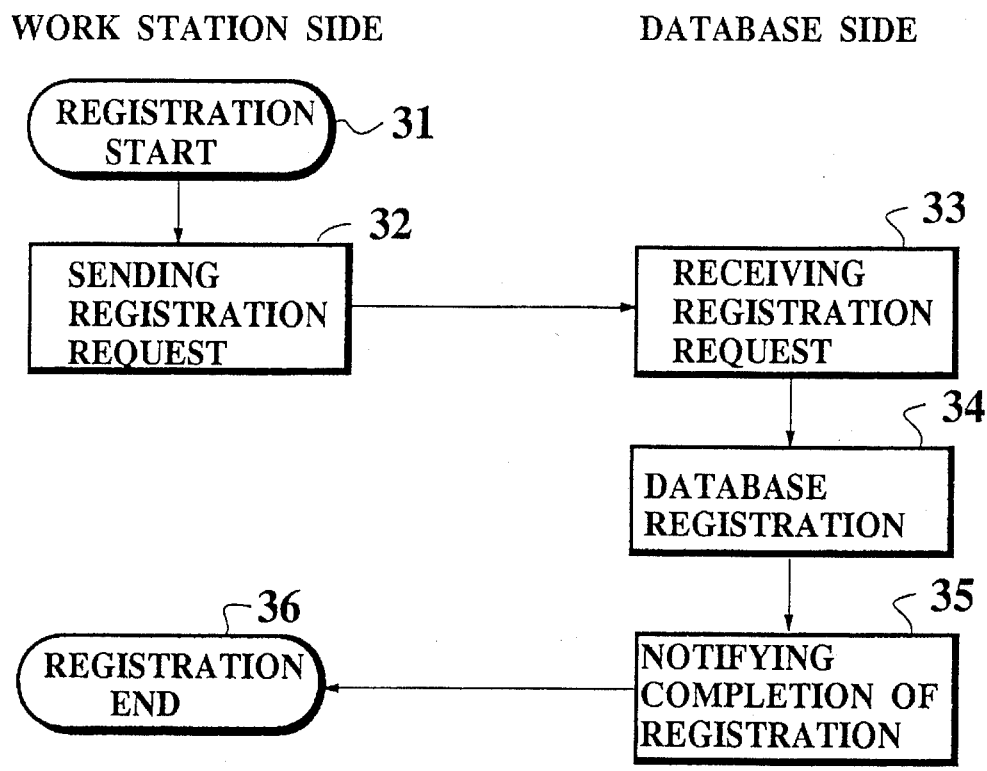
FIG. 4 is a flow chart for the step of database registration in the procedure of image reading according to the flow chart of FIG. 2.
FIG. 5 is an exemplary illustration of one example of a reference data table to be registered in the database in the procedure of database registration according to the flow chart of FIG. 4.

Then, when the registration request is received on the database 3 side at the step 33, and the DBMS registers the produced diagnostic report as well as a reference data table shown in FIG. 5 in which the reference data IDs are listed in correspondence with the ID of the medical examination to which the produced diagnostic report is directed.

Then, the DBMS sends a notification indicating the completion of the registration to the work station 1 at the step 35, and the registration process is ended at the step 36.

Here, the reference data table of FIG. 5 may be generated by automatically recognizing the identification data of the reference data written into the diagnostic report registered in the database 3. For example, the entry in the reference data table of FIG. 5 may be generated by automatically recognizing the reference data IDs in the descriptions in the diagnostic report such as " . . . as can be seen in the front view of the chest portion X-ray image of the medical examination E000294 . . . ", ". . . according to the description in the patient's clinical chart P0001327-C1 . . . "etc.

Alternatively, the reference data table may be generated as shown in FIG. 6 by automatically recording a layout information concerning the order and the image window at which the reference data are displayed in the image display 10 of the work station 1 during the production of the diagnostic report.

There are also other manners of generating the reference data table, as follows.

For example, a work table shown in FIG. 7 can be provided in the work area of the work station 1, where the work table indicates the IDs of the reference data along with the selection flag for indicating the selection made by the radiologist.

Figure 2:
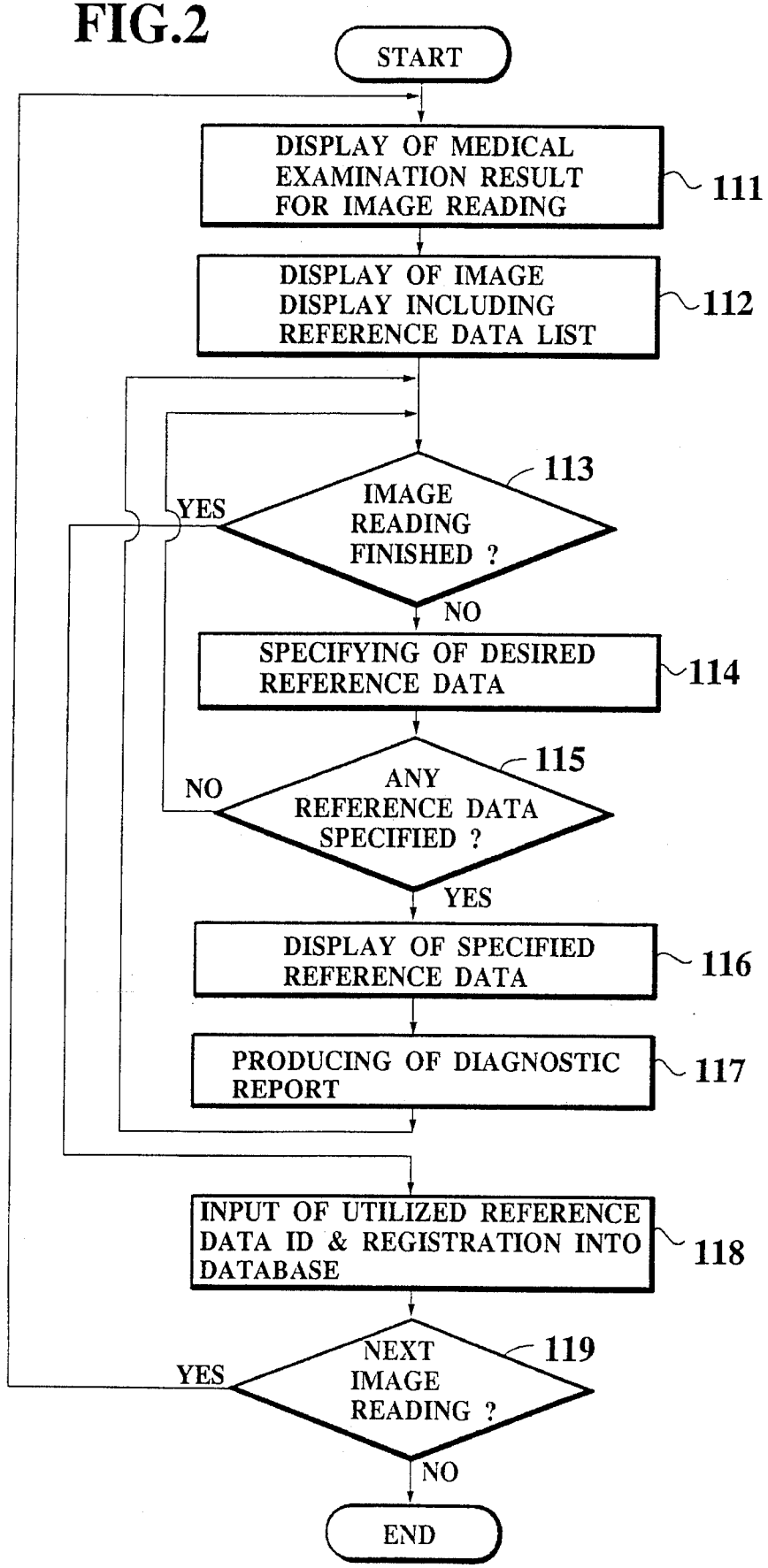
FIG. 2 is a flow chart for a procedure of image reading in the method of managing medical diagnostic data according to the present invention.
Figure 8:
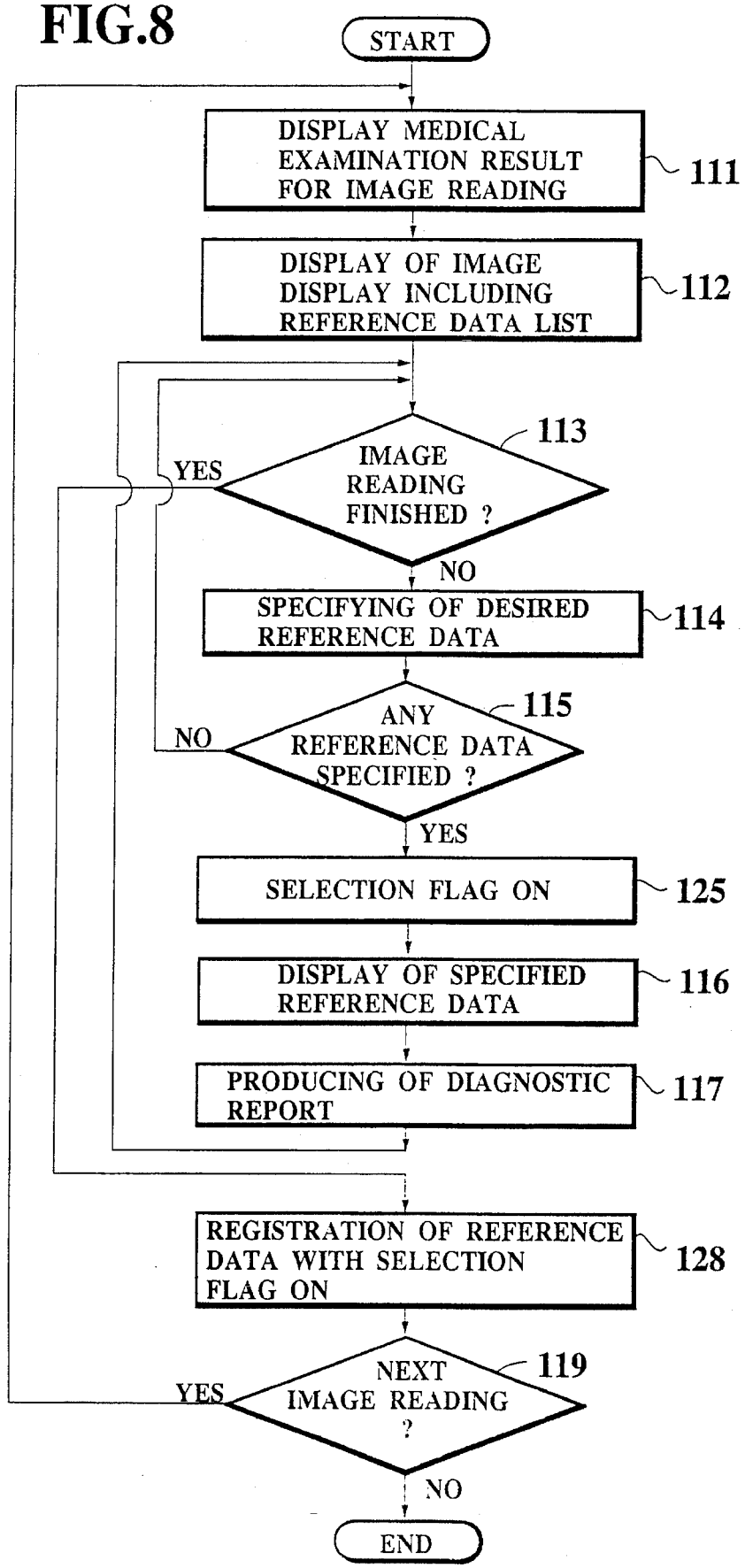
FIG. 8 is a flow chart for a procedure of image reading similar to that of FIG. 2, in a case of utilizing the work table of FIG. 7.

In this case, the flow chart of FIG. 2 should be replaced by the flow chart of FIG. 8, in which there is included the step 125, between the steps 115 and 116, for turning the selection flag ON for the reference data specified by the radiologist at the step 114, and the step 118 is replaced by the step 128 where the the DBMS registers the IDs of only those reference data which have the section flag ON in the work table of FIG. 7 into the reference data table of FIG. 5. The remaining steps of the flow chart of FIG. 8 are substantially identical to the steps of the flow chart of FIG. 2. In FIG. 7, the work table includes the IDs of the reference data used for the same patient in the past at first, among which the radiologist can make the selection of E000294 as indicated in FIG. 7 for example, and the ID of any other reference data searched according to the request from the radiologist is also added to this work table thereafter.

As another example, a work table shown in FIG. 9 can be provided in the work area of the work station 1, where the work table indicates the IDs of the reference data along with the time counter for indicating the length of time for which each reference data is displayed on the image display 10 of the work station 1.

Figure 10:
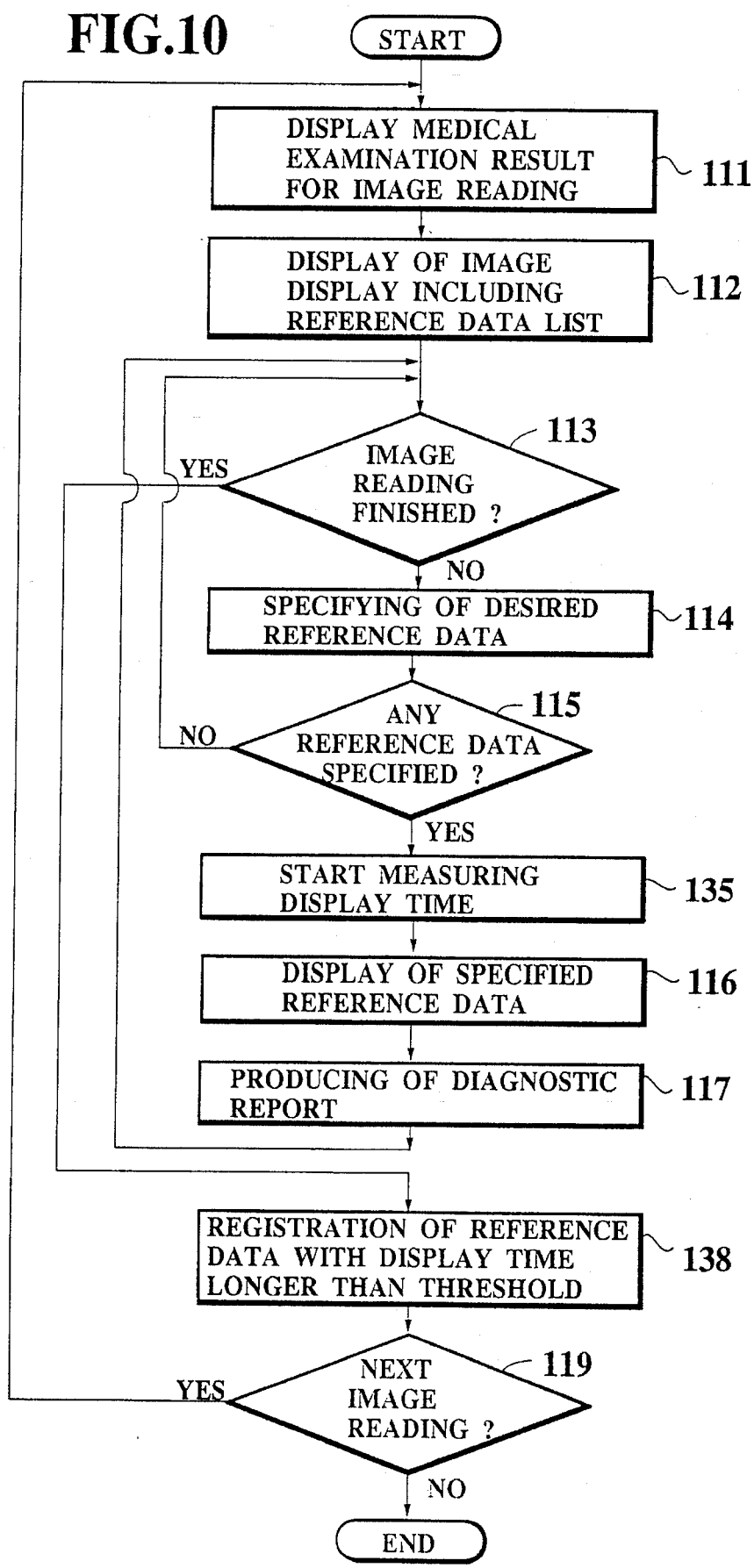
FIG. 10 is a flow chart for a procedure of image reading similar to that of FIG. 2, in a case of utilizing the work table of FIG. 9.

In this case, the flow chart of FIG. 2 should be replaced by the flow chart of FIG. 10, in which there is included the step 135, between the steps 115 and 116, for start measuring the length of time for which each reference data is displayed, and the step 118 is replaced by the step 138 where the the DBMS registers the IDs of only those reference data which have the time counter in the work table of FIG. 9 indicating the time longer than the prescribed threshold time into the reference data table of FIG. 5. Here, the prescribed threshold time can be set equal to 20 seconds. The remaining steps of the flow chart of FIG. 10 are substantially identical to the steps of the flow chart of FIG. 2. In FIG. 9, the work table includes the IDs of all the reference data selected by the radiologist at the step 114, and the time counter counts the cumulative display time of each reference data, by start counting whenever each reference data is displayed on the image display 10 of the work station 1 and stops counting whenever each reference data is erased from the image display 10 of the work station 1.

It is to be noted that the identification data in any format other than the ID formed by a combination of alphabets and numerals used in the above description can be used.

It is also to be noted that the use of the table in a form shown in FIG. 5 is not absolutely necessary, as long as the identification data or the data itself of the reference data can be recorded in correspondence to the identification data or the data itself of the produced data for which the reference data are used.

It is further to be noted that the reference data table may be stored in the system work area of the DBMS or the work area of the work station 1 if possible, instead of the work area of the database 3 as in the above description.

Figure 11:
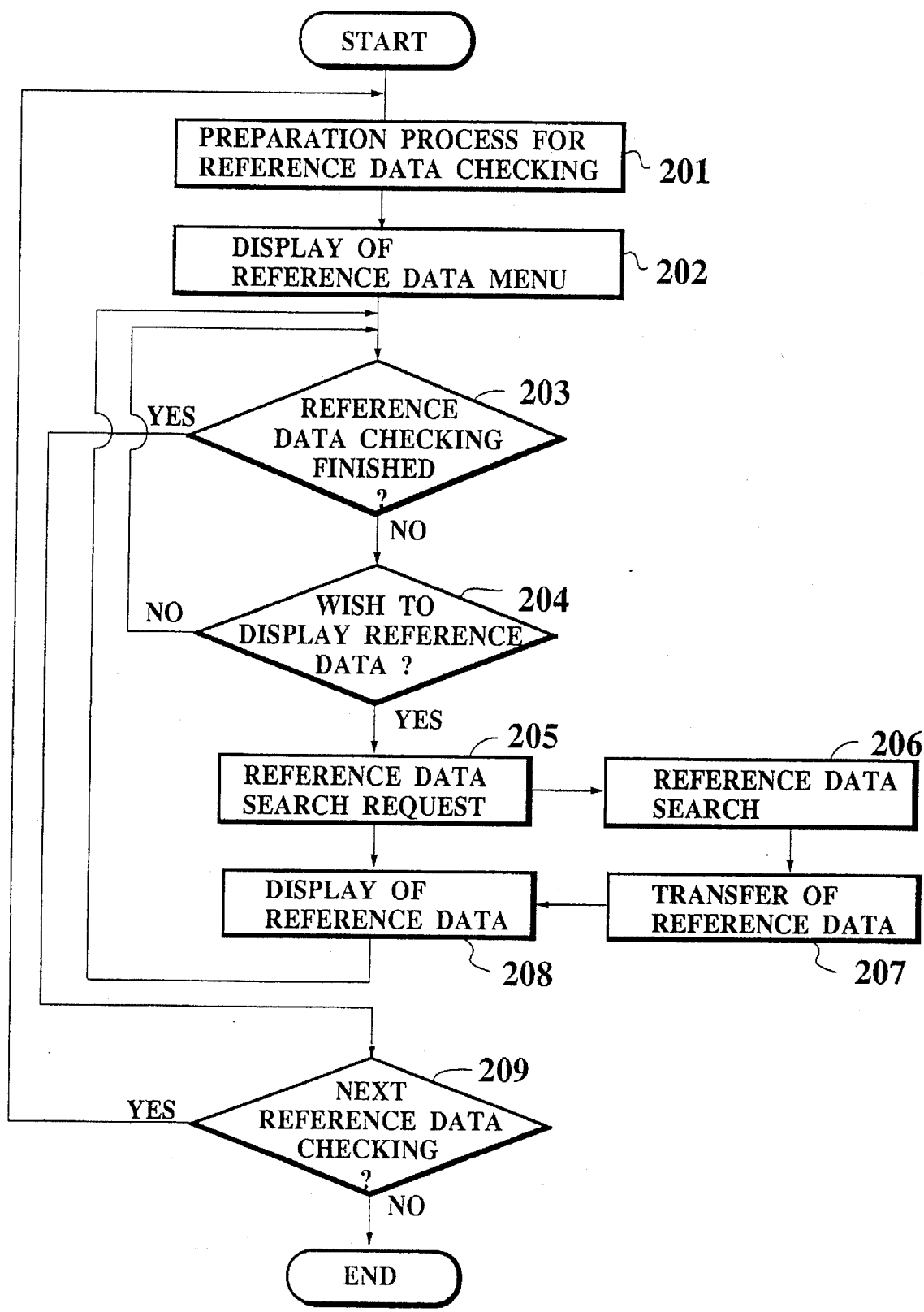
FIG. 11 is a flow chart for a procedure of reference data checking in the method of managing medical diagnostic data according to the present invention.

Next, the reference data checking operation during the image reading of the diagnostic report, on the database sharing network of FIG. 1, is carried out according to the flow chart of FIG. 11, as follows.

As an example, a case in which a physician who requested the radiologist to produce the diagnostic report carries out the reference data checking operation by using this diagnostic report as the base data, during the image reading of the produced diagnostic report at the work station 2, will be considered.

First, at the step 201, a preparation process for the reference data checking to be described in detail below is carried out to produce a reference data menu shown in FIG. 12.

Then, at the step 202, the reference data menu of FIG. 12 is displayed on the work station 2.

Then, at the step 203, whether the reference data checking is finished or not is inquired. In a case the physician indicates that the reference data checking is finished, the process proceeds to the step 209 to be described below, whereas otherwise the process proceeds to the step 204 at which whether the physician wishes to display any reference data enlisted on the reference data menu of FIG. 12. In a case the physician indicates that he wishes to display some reference data, the process proceeds to the step 205, whereas otherwise the process returns to the step 203 described above.

Then, at the step 205, the physician operates the work station 2 to issue a reference data search request for a desired reference data by selecting desired one of the identification data enlisted on the reference data menu of FIG. 12, which is to be sent to the database 3.

In response, at the step 206, the reference data specified by the reference data search request is searched at the database 3, and then the desired reference data found by the search is transferred to the work station 2 at the step 207.

Then, at the step 208, the desired reference data transferred from the database 3 is displayed on the work station 2, and the process proceeds to the step 203 described above.

Finally, when the physician indicates that the reference data checking is finished, next at the step 209, whether the next reference data checking is necessary or not is inquired. In a case the physician indicates that the next reference data checking is necessary, the process returns to the step 201 described above so as to carry out the next reference data checking, whereas otherwise the process terminates.

Figure 13:
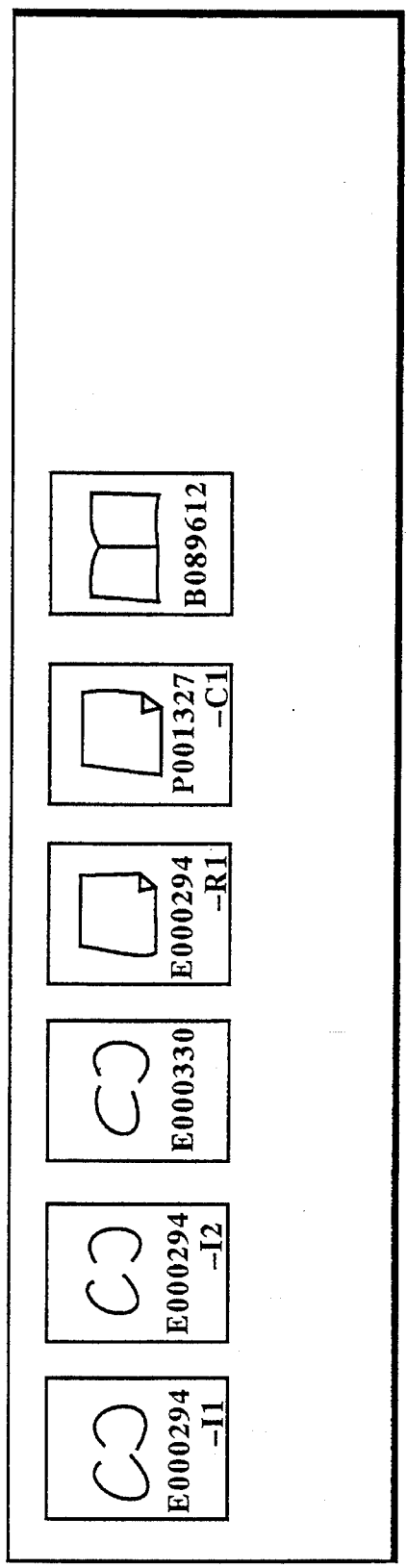
FIG. 13 is an exemplary illustration of another example of a reference data menu to be utilized in the procedure of reference data checking according to the flow chart of FIG. 11.
Figure 14:
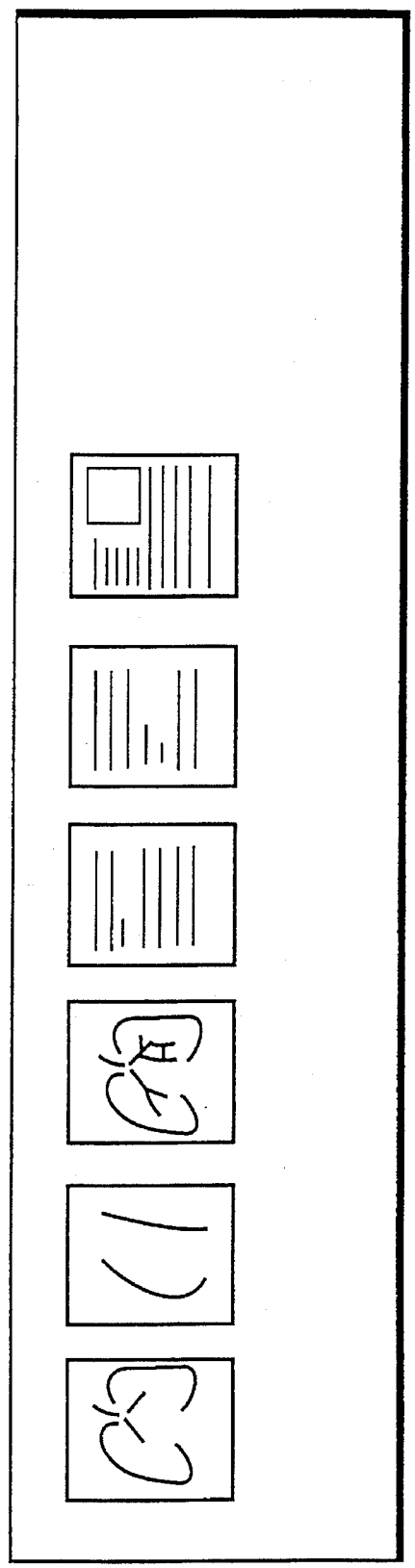
FIG. 14 is an exemplary illustration of still another example of a reference data menu to be utilized in the procedure of reference data checking according to the flow chart of FIG. 11.
Figure 15:
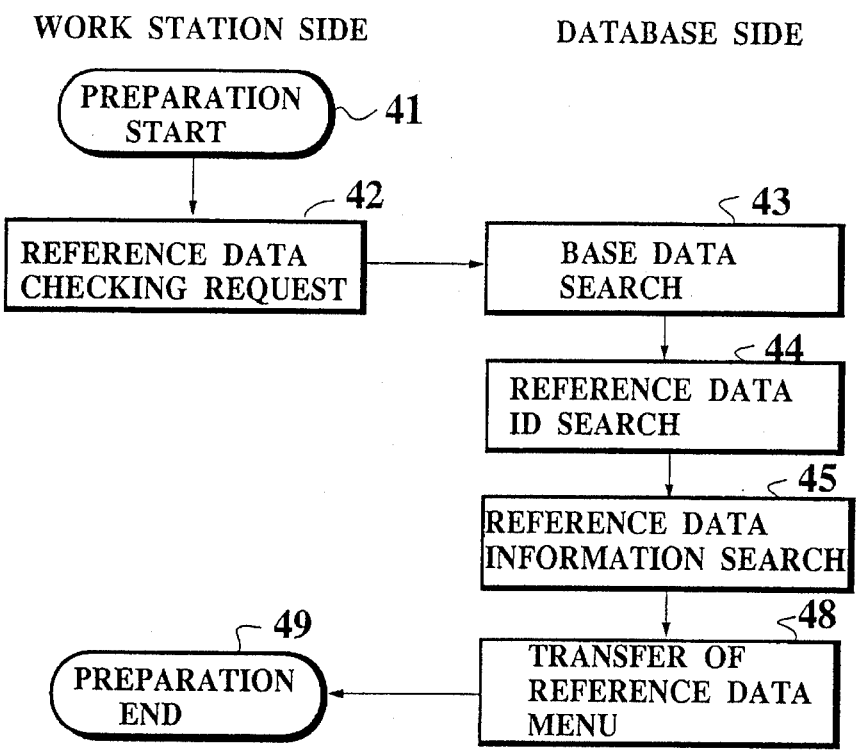
FIG. 15 is a flow chart of one possible procedure for the step of preparation for the reference data checking in the procedure of reference data checking according to the flow chart of FIG. 11.

It is to be noted that the reference data menu of FIG. 12 may be given in a form of icons representing the reference data as shown in FIG. 13, or in a form of contracted images of the reference data themselves as shown in FIG. 14.

In this procedure, at the step 201, the preparation process for the reference data checking can be carried out by any one of the procedures according to the flow charts of FIG. 15 to FIG. 18, as follows.

In a case of the procedure of FIG. 14, as the preparation process starts at the step 41, the reference data checking request specifying the ID of a desired base data whose reference data are to be checked, such as E000513, is sent from the work station 2 side to the database 3 side at the step 42.

Then, in response, the base data specified by the reference data checking request is searched in the database 3 at the step 43, and the IDs of the reference data of the specified base data, such as E000294-I1, E000294-I2, E000294-R1, etc., are searched in the reference data table of FIG. 5 at the step 44.

Then, at the step 45, the information on each of the reference data obtained by the search at the step 44, indicating the name of the data, date of its production, producer of the data, etc. are obtained from the database 3 and temporarily memorized in the work area of the DBMS.

Finally, at the step 48, the reference data menu of FIG. 12 is produced according to the information obtained at the step 45, and transferred to the work area of the work station 2, so as to end the preparation process at the step 49.

Figure 16:
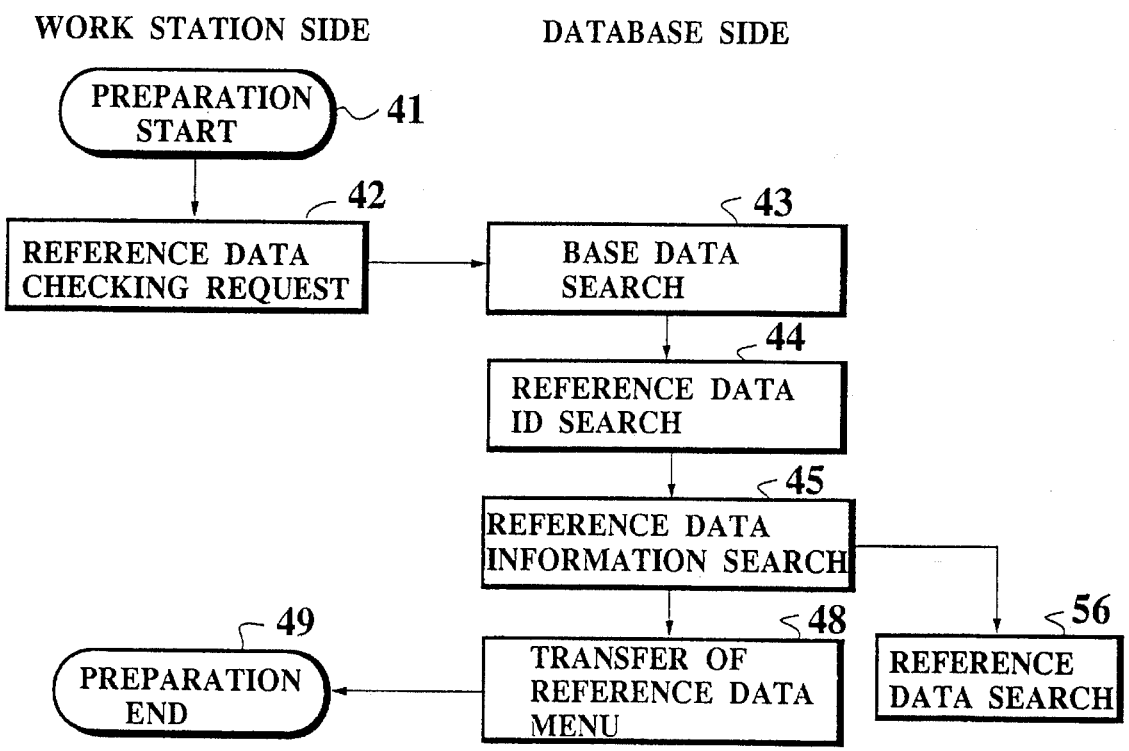
FIG. 16 is a flow chart of another procedure for the step of preparation for the reference data checking in the procedure of reference data checking according to the flow chart of FIG. 11.

In a case of the procedure of FIG. 16, after the search of the reference data information at the step 45, simultaneously with the transfer of the reference data menu at the step 48, the reference data themselves are searched in the database 3 at the additional step 56. The remaining steps of FIG. 16 are substantially identical to those of FIG. 15.

This procedure of FIG. 16 is particularly useful when the database comprises a low speed and large capacity memory device such as an optical disk and the large size data such as image data are involved, as in a case of the medical diagnostic data which include a large number of image data such as the X-ray images and the tomographic images. This is because, in this procedure, the reference data themselves can be transferred to a high speed memory such as a hard disk from the low speed optical disk in advance, such that the appropriate reference data can be transferred to the work station as soon as the reference data search request is received from the work station, and therefore the reference data checking operation as a whole can be carried out more efficiently.

Figure 17:
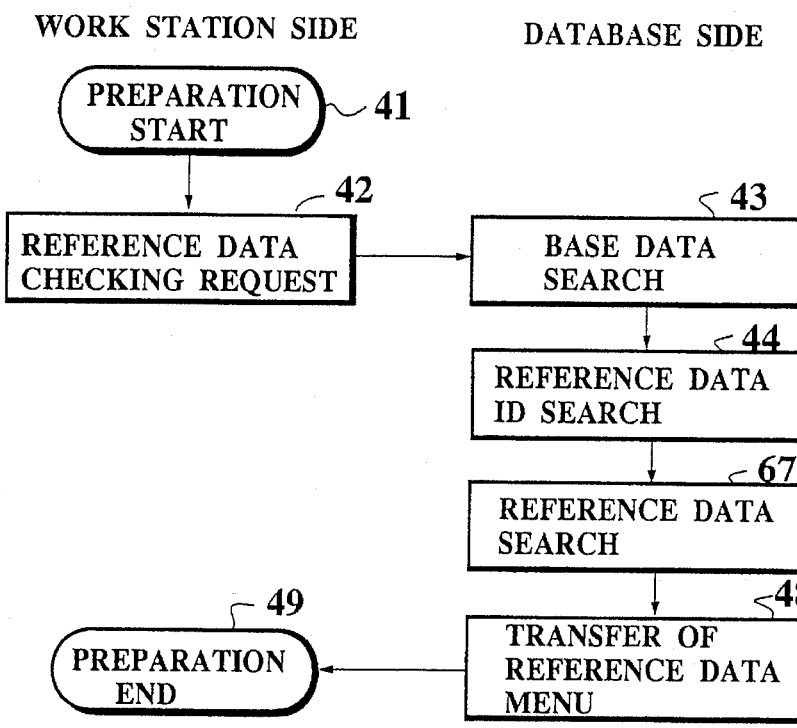
FIG. 17 is a flow chart of still another possible procedure for the step of preparation for the reference data checking in the procedure of reference data checking according to the flow chart of FIG. 11.

In a case of the procedure of FIG. 17, instead of the search of the reference data information at the step 45, before the transfer of the reference data menu at the step 48, the reference data themselves are searched in the database 3 and transferred to the work area of the work station 2 at the step 67. The remaining steps of FIG. 17 are substantially identical to those of FIG. 15.

In this procedure of FIG. 17, the display of the appropriate reference data on the work station can be realized as soon as the reference data search request is issued, and therefore the reference data checking operation as a whole can be carried out more efficiently and with less frustration caused in the physician.

In such a procedure, when the reference data table in a form shown in FIG. 6 is used, the order and the image window at which the reference data are to be displayed in the image display 10 of the work station 2 can be automatically controlled according to the reference data table of FIG. 6. Alternatively, the order and the image window at which the reference data are to be displayed may be specified by the physician himself.

Figure 18:
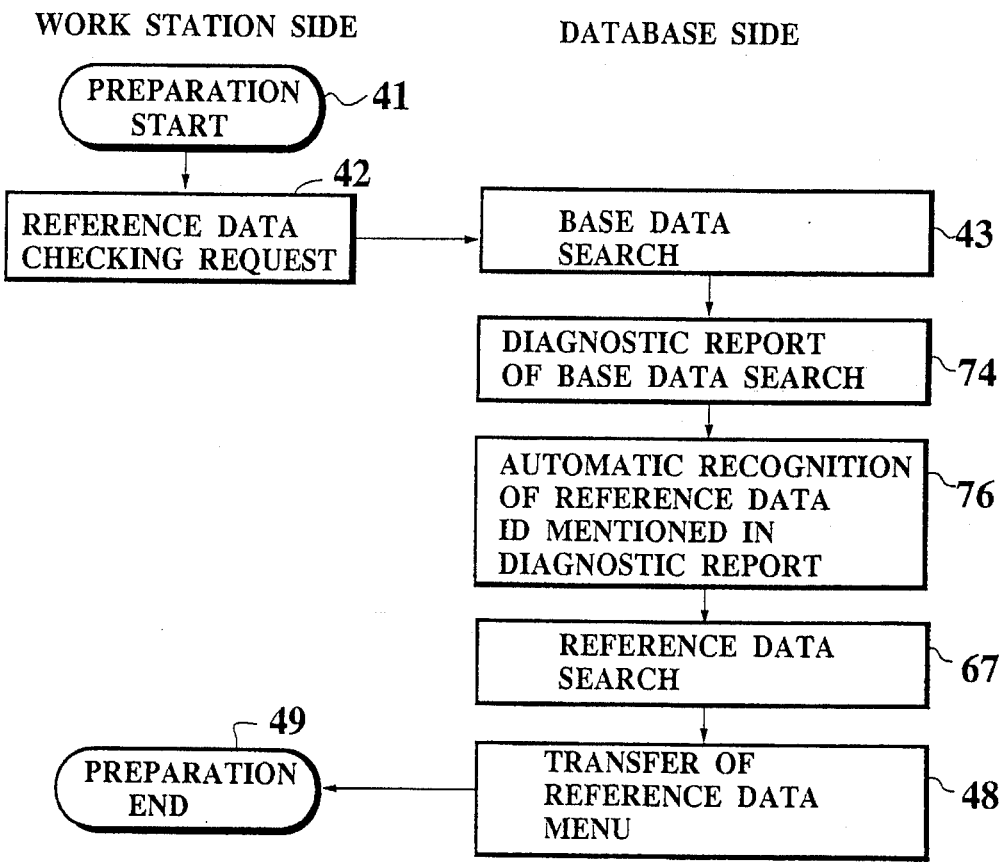
FIG. 18 is a flow chart of yet another procedure for the step of preparation for the reference data checking in the procedure of reference data checking according to the flow chart of FIG. 11.

In a case of the procedure of FIG. 18, instead of the search of the reference data IDs at the step 44, the ID of the diagnostic report of the specified base data is searched in the database 3 at the step 74, and the IDs of the reference data mentioned in that diagnostic report are automatically recognized at the step 76. The remaining steps of FIG. 18 are substantially identical to those of FIG. 17, such that the reference data menu is produced according to the IDs automatically recognized at the step 76.

It is to be noted that the preparation process for the reference data checking according to any one of the flow charts of FIG. 15 to FIG. 18 may be carried out in advance, in a case the execution of the reference data checking operation is scheduled in advance to a specific time, so as to further improve the efficiency of the utilization of the DBMS in the database 3.

Figure 19:
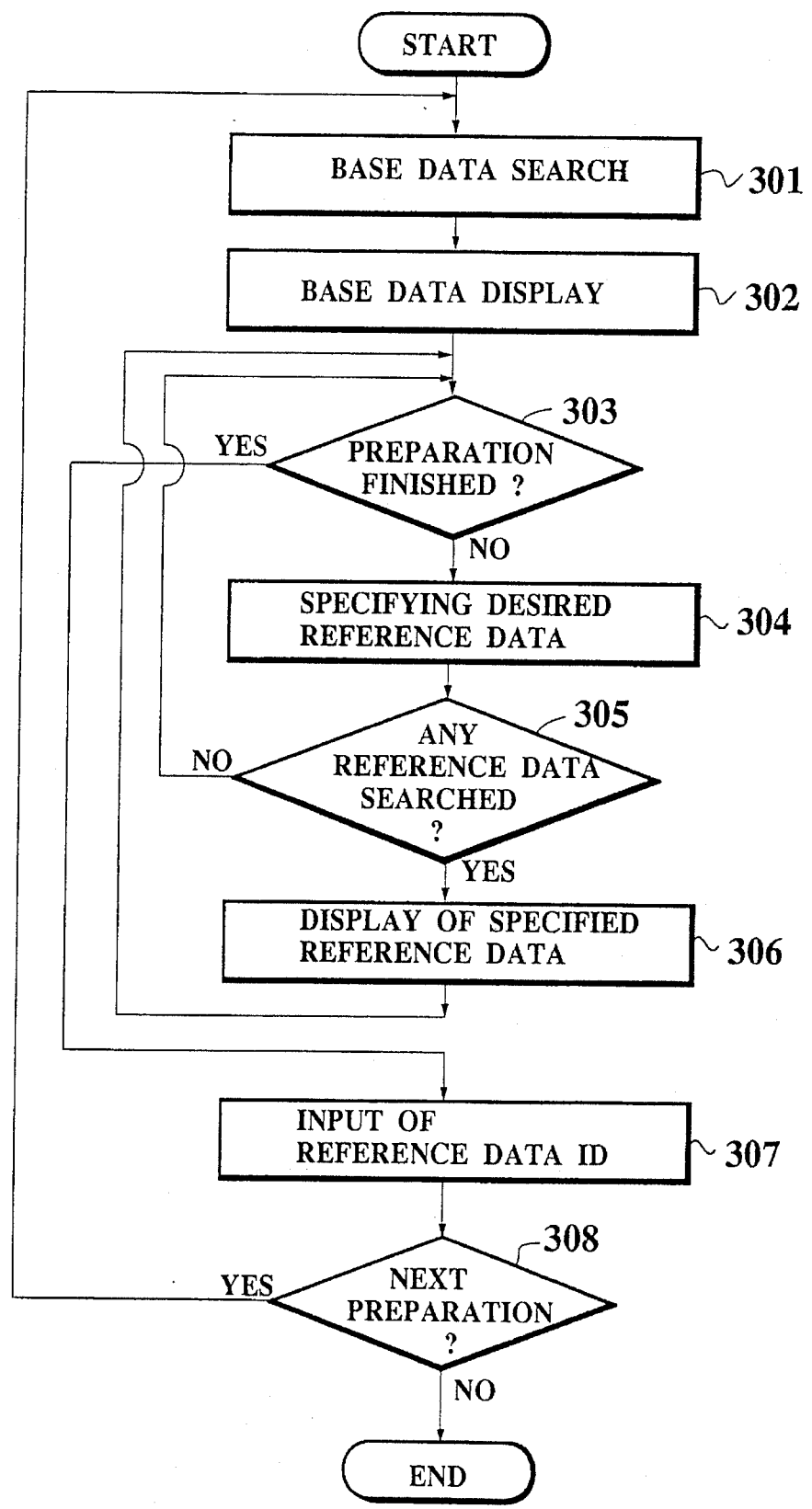
FIG. 19 is a flow chart for a procedure of conference preparation in the method of managing medical diagnostic data according to the present invention.

Now, similarly to the flow chart of FIG. 2 described above, a conference preparation to be made by a host doctor of the conference among the doctors, on the database sharing network of FIG. 1, can be carried out according to the flow chart of FIG. 19, as follows.

In this case, first at the step 301, the host doctor specifies one particular medical examination as the base data and this specified base data is searched in the database 3, and then the searched out base data is displayed on the work station of the host doctor.

Then, at the step 303, whether the conference preparation is finished or not is inquired. In a case the host doctor indicates that the conference preparation is finished, the process proceeds to the step 306 to be described below, whereas otherwise the process proceeds to the step 304 at which the host doctor specifies a desired reference data either by selecting desired one of the identification data enlisted on a list of the reference data displayed on the work station of the host doctor or by entering the identification data of the desired reference data so as to request the search of the desired reference data in the database 3.

Then, at the step 305, whether any reference data is specified at the step 304 or not is determined. In a case there is no reference data specified at the step 114, the process proceeds to the step 303 described above, whereas otherwise the process proceeds to the step 306 at which the DBMS controls the database sharing network of FIG. 1 to carry out the requested search in the database 3 and display the desired reference data specified at the step 304 on the work station of the host doctor. The process then returns to the step 303 described above.

Then, when the host doctor indicates that the conference preparation is finished at the step 303, next at the step 307, the host doctor inputs the IDs of the reference data to be actually utilized in the conference, and in response the DBMS registers the IDs of the reference data in correspondence with the ID of the base data specified at the step 301 into the database 3.

Finally, at the step 308, whether the next conference preparation is necessary or not is inquired. In a case the host doctor indicates that the next conference preparation is necessary, the process returns to the step 301 described above so as to carry out the next conference preparation, whereas otherwise the process terminates.

It is to be noted that in the procedure of the conference preparation described above, the list of the reference data to be used at the step 304 can be produced in any one of the manners similar to those of the flow charts of FIG. 8 and FIG. 10 described above for the case of the image reading.

Figure 20:
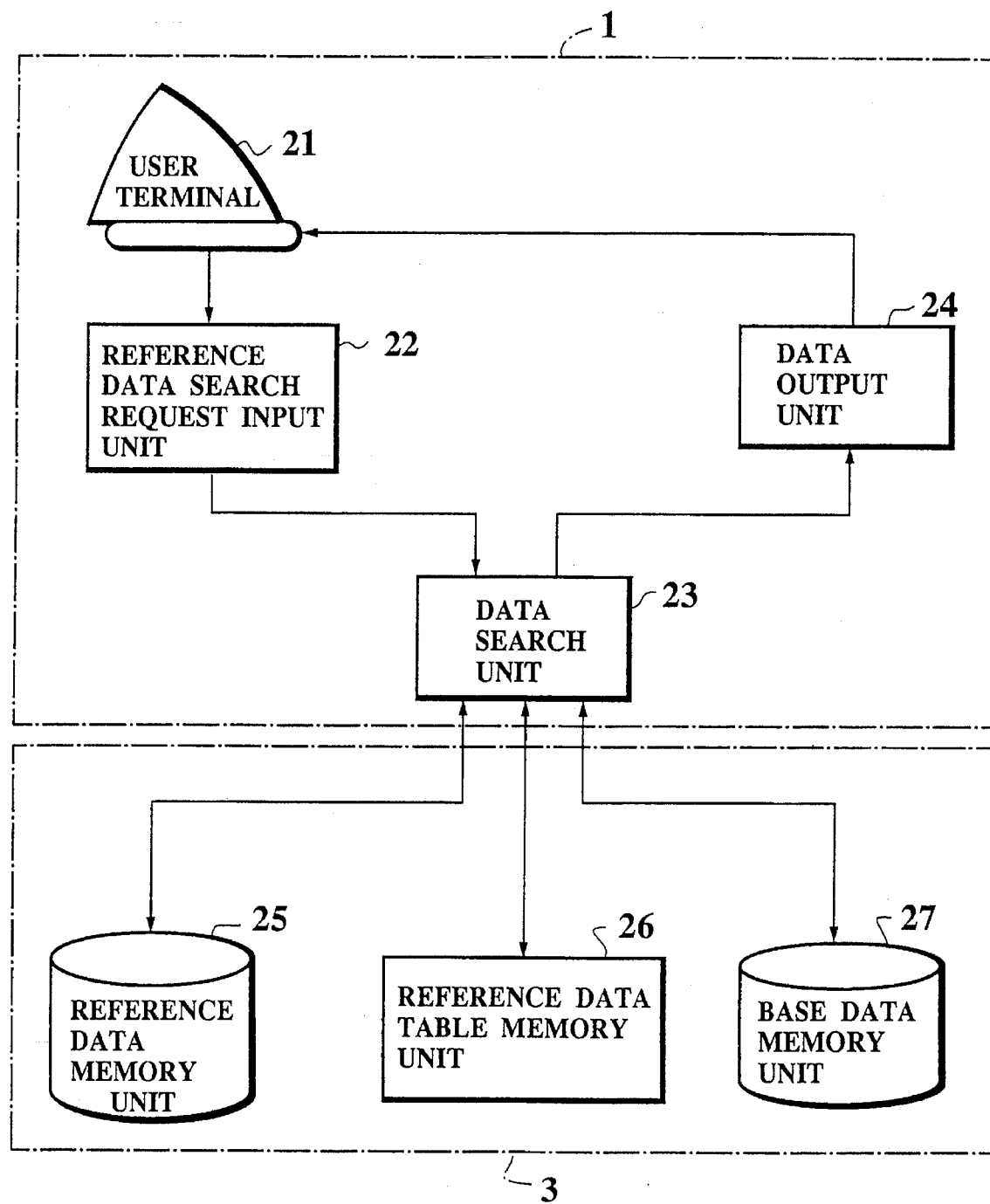
FIG. 20 is a block diagram of a main portion of the database sharing network of FIG. 1.

Now, as shown in FIG. 20, the work station 1 in the database sharing network of FIG. 1 has a configuration including: a user terminal 21 on which the base data, the reference data, and the reference data menu are presented to the user in a manner described above, and from which the user makes a request for the reference data checking of a specific reference data; a reference data search request input unit 22 for generating a reference data searching request according to the request for the reference data checking made by the user at the user terminal 21; a data search unit 23 for conducting a search in the database 3 for the base data and the reference data menu to be presented at the user terminal 21, as well as the specific reference data requested by the reference data search request supplied from the reference data search request input unit 22; and a data output unit 24 for outputting the base data, the reference data menu, and the specific reference data searched by the data search unit 23 and to be presented to the user on the user terminal 21.

On the other hand, also as shown in FIG. 20, the database 3 in the database sharing network of FIG. 1 has a configuration including: a reference data memory unit 25 for storing the reference data; a reference data table memory unit 26 for storing the reference data table such as that shown in FIG. 5 of FIG. 6; and the base data memory unit 27 for storing the base data; all of which can be accessed from the data search unit 23.

As described, according to the present invention, it becomes possible to provide a method of managing medical diagnostic data in a database system such as a database sharing network, in which the data look up operation to be made at a user terminal while working on a currently interested medical diagnostic data is simplified as there is no need to repeat the operation to enter the identification code of the same reference data. Consequently, the doctor using the database system can conduct the diagnostic session more efficiently, especially when the diagnostic session requires the repetitive data look up operations.

In addition, according to the present invention, the database system can also be used effectively for the preparation of the conference as described above.

Furthermore, the method of managing medical diagnostic data in a database system according to the present invention can easily be implemented in the existing database system such as a database sharing network, regardless of the number of user terminals and the capacity of the database.

It is to be noted that the method as described above can be used hierarchically, such that a medical examination B which is a reference data of another medical examination A can have still another medical examination C as its reference data, and so on.

It is also to be noted that the set of reference data for a particular base data may be different for the difference circumstances, so that it is possible to use the different sets of reference data for a case of the image reading and a case of the conference preparation, etc. as well as the different sets of reference data for different users.

It is further to be noted that the base data is not limited to the medical examination as in the above description, and any data stored in the database can be utilized as the base data or the reference data, according to the need.

Besides these, many modifications and variations of the above embodiments may be made without departing from the novel and advantageous features of the present invention. Accordingly, all such modifications and variations are intended to be included within the scope of the appended claims.

What is claimed is:

1. A method of managing medical diagnostic data in a database system having a database, a user terminal, and search means for searching the database in response to a request for a presentation of data in the database from the user terminal, comprising the steps of:

(a) storing a plurality of medical diagnostic data, in said database;

(b) specifying at the user terminal one of the medical diagnostic data that was stored in the database at step (a) as a base data from which reference data that are relevant to the base data are to be looked up;

(c) specifying at the user terminal a desired number of the medical diagnostic data that were stored in the database at step (a) as the reference data that are relevant to the base data that was specified at step (b) and that are to be looked up for the base data specified at step (b);

(d) storing identification data for the base data that was specified at step (b) in correspondence with identification data for the reference data that were specified at step (c), in the database;

(e) presenting a requested base data on the user terminal along with identification data for specific reference data that were stored in the database in correspondence with identification data of the requested base data at step (d), by automatically searching the database with the search means for the requested base data and the identification data of the reference data in response to each request for presentation of the requested base data made from the user terminal;

(f) specifying at the user terminal a specific identification data for a desired one of the reference data that were presented along with the requested base data on the user terminal; and (g) presenting the desired one of the reference data corresponding to said specific identification data that was specified at step (f) on the user terminal by automatically searching the database with the search means for the desired one of the reference data in response to each request for presentation of the desired one of the reference data requested from the user terminal.

2. The method of claim 1, wherein at step (d), the identification data of the base data and the identification data of the reference data are stored in a form of a reference data table enlisting each of the identification of the reference data in correspondence with the identification data of the base data.

3. The method of claim 2, wherein at step (d), the reference data table further indicates a layout information concerning order and positions of the reference data in a presentation on the user terminal at step (g).

4. The method of claim 1, wherein at step (c), the desired number of the medical diagnostic data are specified by utilizing a work table enlisting the identification data of the medical diagnostic data stored in the database along with flags for indicating the identification data of those medical diagnostic data enlisted in the work table which are specified as the reference data at the user terminal.

5. The method of claim 1, wherein at step (c), the desired number of the medical diagnostic data are specified by utilizing a work table enlisting the identification data of the medical diagnostic data stored in the database along with time counters for indicating a length of time for which each of the medical diagnostic data is presented on the user terminal in a process of specifying the reference data, where those medical diagnostic data whose identification data are enlisted in correspondence with the time counters indicating the length of time longer than a prescribed threshold length are in the work table are regarded as specified as the reference data.

6. The method of claim 1, wherein at step (c), the desired number of the medical diagnostic data are specified by automatically recognizing and recording the identification data of the medical diagnostic data mentioned in the base data.

7. The method of claim 1, wherein at step (e), the identification data of the reference data stored in correspondence with the identification data of the data base at step (d) are presented in a form of a reference data menu enlisting the identification data of the reference data, and wherein at step (f), said one of the identification data for the desired one of the reference data is specified by selecting a desired one entry on the reference data menu.

8. The method of claim 7, wherein the reference data menu enlists the identification data of the reference data in forms of icons.

9. The method of claim 7, wherein the reference data menu enlists the identification data of the reference data in forms of contracted images of the reference data.

10. The method of claim 1, further comprising the steps, to be carried out before step (g), of:

(1) searching the reference data stored in correspondence with the base data at step (d) in the database.

11. The method of claim 10, wherein the step (1) is carried out in parallel to the step (e), and which further comprises the step to be carried out between the steps (f) and (g) of:

(2) transferring the desired one of the reference data corresponding to said one of the identification data specified at step (f) among the reference data searched out at step (1) from the database to the user terminal, such that the desired one of the reference data can be presented on the user terminal at step (g) as soon as said one of the identification data is specified at step (f).

12. The method of claim 10, wherein the steps (1) is carried out between the steps (d) and (e), and which further comprises the step to be carried out between the steps (1) and (e) of:

(2) transferring the reference data searched out at step (1) from the database to the user terminal, such that the desired one of the reference data can be presented on the user terminal at step (g) as soon as said one of the identification data is specified at step (f).

13. The method of claim 1, further comprising the steps, to be carried out before step (g), of:

(i) automatically recognizing the identification data of the medical diagnostic data mentioned in the base data presented at step (e) as the reference data, and searching these reference data in the database;

(ii) transferring the reference data searched out at the step (i) from the database to the user terminal.

14. An apparatus for managing medical diagnostic data in a database system, comprising:

a database for storing medical diagnostic data, wherein one of the medical diagnostic data stored in the database is specified as a base data from which reference data that are relevant to the base data are to be looked up, a desired number of the medical diagnostic data stored in the database are specified as reference data that are relevant to the base data and are to be looked up from the base data;

reference data table means for storing identification data for the base data that are stored in the database in correspondence with identification data for the reference data that are stored in the database;

means for requesting a presentation of base data that are stored in the database;

means for searching the database for a requested base data that is requested by said means for requesting, and for searching the reference data table means for identification data of the reference data that are relevant to the requested base data and are to be looked up from the requested base data; and means for presenting the requested base data that was found by said means for searching, along with the identification data of the relevant reference data that were found by said means for searching, in response to each request for the presentation of the requested base data made by said means for requesting.

15. The apparatus of claim 14, wherein the reference data table means further stores a layout information concerning order and positions of the reference data in a presentation by said means for presenting along with the identification data of the base data and the reference data, and said means for presenting also presents the layout information along with the base data and the identification data of the reference data.

* * * * *